United States Patent
Khan et al.

(10) Patent No.: US 10,294,124 B2
(45) Date of Patent: May 21, 2019

(54) METHOD AND APPARATUS FOR LIQUID DISINFECTION BY LIGHT EMITTED FROM LIGHT EMITTING DIODES

(71) Applicant: Atlantium Technologies Ltd, Beit-Shemesh (IL)

(72) Inventors: Benjamin Khan, Beit Yanai (IL); Michael Kertser, Bney Aish (IL); Zohar Vardiel, Or Yehuda (IL); Ytzhak Rozenberg, Ramat Gan (IL)

(73) Assignee: Atlantium Technologies Ltd., Beit-Shemesh (IL)

( * ) Notice: Subject to any disclaimer, the term of this patent is extended or adjusted under 35 U.S.C. 154(b) by 0 days.

(21) Appl. No.: 14/343,054

(22) PCT Filed: Jan. 23, 2014

(86) PCT No.: PCT/IL2014/050083
§ 371 (c)(1),
(2) Date: Mar. 6, 2014

(87) PCT Pub. No.: WO2014/115146
PCT Pub. Date: Jul. 31, 2014

(65) Prior Publication Data
US 2015/0314024 A1 Nov. 5, 2015

Related U.S. Application Data

(60) Provisional application No. 61/755,984, filed on Jan. 24, 2013.

(51) Int. Cl.
*C02F 1/32* (2006.01)
*A61L 2/10* (2006.01)
*F21Y 107/10* (2016.01)

(52) U.S. Cl.
CPC ............ *C02F 1/325* (2013.01); *A61L 2/10* (2013.01); *C02F 2201/3222* (2013.01);
(Continued)

(58) Field of Classification Search
None
See application file for complete search history.

(56) References Cited

U.S. PATENT DOCUMENTS 6,022,459 A * 2/2000 Briggs .................. C02F 1/4606
204/228.4
7,520,978 B2 4/2009 Harbors
(Continued)

FOREIGN PATENT DOCUMENTS

| CN | 101215017 | 7/2008 |
|---|---|---|
| CN | 101588994 | 11/2009 |

(Continued)

OTHER PUBLICATIONS

Search Report dated Jan. 9, 2019 from counterpart application No. EP17194829.2.

*Primary Examiner* — James Choi
(74) *Attorney, Agent, or Firm* — Pearl Cohen Zedek Latzer Baratz LLP

(57) ABSTRACT

An ultraviolet (UV) liquid treatment apparatus is disclosed. The apparatus may include a conduit having an inlet to receive liquid to be treated and an outlet to discharge treated fluid, the conduit defining a plurality of liquid flow paths between the inlet and the outlet. The apparatus may further include an UV light emitting diode (LED) module array to illuminate the liquid, wherein the UV LED module array comprises a plurality of UV LED modules arranged on a curved surface of an array holder, such the UV LED module array is configured to generate a customized spatial light flux (Continued)

distribution within the conduit that matches the liquid flow paths so as to obtain a desired UV dose distribution.

11 Claims, 13 Drawing Sheets

(52) U.S. Cl.
CPC ........... *C02F 2201/3227* (2013.01); *C02F 2201/3228* (2013.01); *C02F 2303/04* (2013.01); *F21Y 2107/10* (2016.08)

(56) References Cited

U.S. PATENT DOCUMENTS

| | | | |
|---|---|---|---|
| 8,324,595 | B2 | 12/2012 | Takahashi et al. |
| 2001/0046652 | A1* | 11/2001 | Ostler ............ A61C 19/004 433/29 |
| 2003/0086848 | A1 | 5/2003 | Saccomanno |
| 2004/0222163 | A1 | 11/2004 | Saccomano |
| 2006/0283786 | A1* | 12/2006 | Harbers ............ A61L 9/20 210/85 |
| 2007/0272877 | A1* | 11/2007 | Tribelsky ............ A61L 2/10 250/431 |
| 2010/0264329 | A1* | 10/2010 | Vardiel ............ C02F 1/325 250/436 |
| 2010/0320147 | A1* | 12/2010 | McGuire ............ E21B 43/26 210/638 |
| 2011/0022696 | A1 | 1/2011 | Bardsley |
| 2011/0226966 | A1* | 9/2011 | Takahashi ............ A01K 63/04 250/492.1 |
| 2014/0117250 | A1 | 5/2014 | Vardiel et al. |

FOREIGN PATENT DOCUMENTS

| | | |
|---|---|---|
| CN | 202201732 | 4/2012 |
| CN | 102198964 | 1/2013 |
| JP | H09-038192 | 2/1997 |
| JP | H09-038503 | 2/1997 |
| JP | H11-087770 | 3/1999 |
| JP | 2004 050174 | 2/2004 |
| JP | 2005-508228 | 3/2005 |
| JP | 2006-346676 | 12/2006 |
| WO | WO/2007/113537 | 10/2007 |
| WO | WO/2008/059503 | 5/2008 |
| WO | WO/2010/058607 | 5/2010 |
| WO | WO 2010/058607 | 5/2010 |
| WO | WO 2010/071814 | 6/2010 |

* cited by examiner

METHOD AND APPARATUS FOR LIQUID DISINFECTION BY LIGHT EMITTED FROM LIGHT EMITTING DIODES

CROSS REFERENCE TO RELATED APPLICATIONS

This application is a National Phase Application of PCT International Application No. PCT/IL2014/050083, International Filing Date Jan. 23, 2014, claiming priority of U.S. Provisional Patent Application No. 61/755,984, filed Jan. 24, 2013 which is hereby incorporated by reference.

BACKGROUND

Ultraviolet (UV) liquid disinfection systems have been long known, utilizing UV light to inactivate microorganisms. Higher inactivation levels are achieved with higher UV dose values. Light Emitting Diodes (LED's) are well known for having a high luminous efficiency and for being highly-reliable light sources. LED modules or LED chips are also known for their high switching rates, meaning that a LED module may be instantly lightened and instantly turned off. Each LED element includes a module (i.e. a chip or a die) of semiconductor wafer doped to form a plurality of diodes designed to emit light when electrically powered. The wavelength in which light is emitted from a LED depends on the semiconductor crystal included in the LED module. Various LED modules may emit light at wavelengths from the infrared to the ultraviolet (200 nm-850 nm). UV LED modules are mercury-free, which makes them suitable for treating drinking water.

Since most LED modules have low lightening intensity and require a low amount of energy relative to other light sources, such as medium pressure UV lamps, it would be beneficial to use as many modules as possible in a single lightening device. LED modules for example, in the range of the UV germicidal spectrum (200-320 nm), are usually grouped together in the form of a LED array. Previous attempts to disinfect water using LED as a light source were only partially successful. Commercial UV LED-based disinfection systems are limited to disinfecting small amounts of water, due to the limited lightening intensity of the LED modules.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
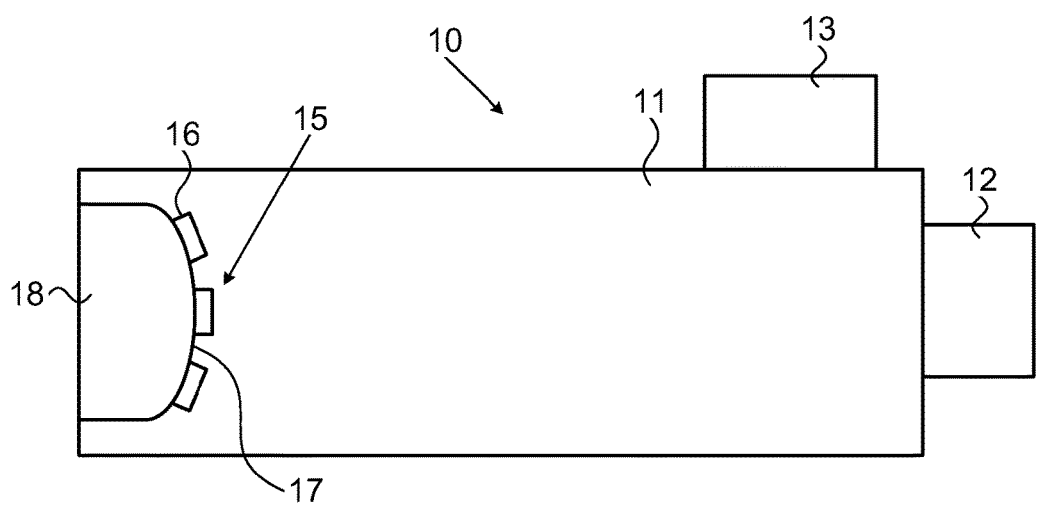
FIG. 1 is a high level illustration of an exemplary UV liquid treatment apparatus according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF SOME EMBODIMENTS

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In some embodiments, the liquid to be treated may be held in a reservoir, for example a reservoir of a municipal water supply system, a water purification tank, etc. The liquid (e.g., water) in the reservoirs may be contaminated by a secondary contamination due to the liquid holding time in the reservoir.

A liquid disinfection and/or treatment process according to some embodiments of the invention, may include inactivation or removal of organism, bacteria, microorganism, being, creature, microbe, germ, virus, organic contaminator, non-organic contaminator, oxidizeable toxic or contaminator; cumulative noxious species of biological or chemical origin, oxidizing particle, fragment or element, e.g., hydrogen peroxide or titanium dioxide, intended to oxidize a contaminator and/or the like. Some demonstrative embodiments of the invention may refer to using ultraviolet (UV) light to disinfect the liquid and/or to oxidize particles within the liquid.

In liquid disinfection, it may be necessary to apply light in a wavelength capable of inactivating microorganisms (e.g., 200 nm-320 nm) to instantly illuminate the liquid, for example, when water starts to flow in a pipe or a conduit upon opening of a water faucet. An optional solution may be to continuously operate a light emitting source for example, a UV lamp. A continuous mode of operation, however, is energetically inefficient and may increase the rate of formation of deposit (e.g., contamination) on an internal surface of the conduit that may result in an emission of byproducts, such as converting $NO_3$ to $NO_2$. Another option may be to use a light source that could be instantly activated, for example, light emitting diodes (LED's).

According to embodiments of the invention, one or more LED modules may be used as the light source for liquid disinfection and may be included in an UV liquid treatment apparatus. Each UV LED module (also known in the art as "die)" may include a plurality of LED's arranged in an array located on a semiconductor wafer. The LED modules may be arranged in one or more arrays customized to increase the efficiency of the liquid disinfection process. Some LED modules are configured to emit light in wavelength capable of inactivating microorganisms. For example, LED modules including aluminum nitride (AlN) and gallium nitride (GaN) crystals (e.g., semiconductor wafers) may emit UV light at wavelengths in the germicidal range (e.g., around 200-320 nm). Each LED module may be connected to a standard TO-3 semiconductor package. The LED modules may be installed such that each of the LED modules is connected to a separate power source. Additionally or alternatively, an array of LED modules may be installed such that a single power source may feed more than one LED module.

The LED modules may be positioned externally to a conduit or vessel carrying the liquid. Alternatively, the LED modules may be positioned within the conduit. The UV LED module array may be arranged on surface of an array holder. In some embodiments, the surface of the array holder may be curved. In some embodiments, the LED modules may be placed or located on the curved surface such that a customized spatial light flux distribution is generated within the conduit. The customized spatial light flux distribution may produce a UV dose with a desired dose distribution function, as to increase the efficiency of the UV disinfection treatment of the liquid in the conduit.

Reference is made to FIG. 1, which is an illustration of an exemplary UV liquid treatment apparatus according to some demonstrative embodiments of the invention. An apparatus 10 may include a conduit 11 for carrying the liquid, an inlet 12 to receive liquid to be treated and an outlet 13 to discharge treated fluid. Conduit 11 may be designed to define a plurality of liquid flow paths between inlet 12 and the outlet 13. Apparatus 10 may further include a UV LED module array 15 comprising a plurality of UV light emitting diode (LED) modules 16. UV LED array 15 may be arranged on a curved surface 17 of an array holder 18 to generate a customized spatial light flux distribution within the conduit that produces a UV dose with a desired dose distribution function.

Conduit 11 may include any material suitable for carrying liquids, for example, stainless steel, quarts, various polymers, etc. In some embodiments, conduit 11 may include material transparent to UV light or may be, at least partially, coated with a coating that reflects UV light. A conduit 11 according to the invention may have any cross section, dimensions and geometry that are designed to support the defined plurality of liquid flow paths between inlet 12 and outlet 13.

UV LED module array 15 may include two or more UV LED modules 16. Each of modules 16 may include a plurality (e.g., an array) of light emitting diodes (LED's) located on a semiconductor wafer. Modules 16 may be located at a predetermined array on curved surface 17 of array holder 18. Curved surface 17 may be, for example, a concave or a convex surface, round or conic. In some embodiments, surface 17 may be another type of non-flat surface, for example a pyramidal surface. In alternative embodiments, UV LED module array 15 may be positioned on a substantially planar or flat surface of the array holder. The location of each module 16 on surface 17 may be determined such that a customized spatial light flux distribution may be generated within conduit 11 to produce a UV dose with a desired dose distribution. Additionally or alternatively, the dimensions of curved surface 17 may be determined according to the customized spatial light flux distribution.

Reference is now made to FIGS. 2-4, which demonstrate some exemplary embodiments, in which the disinfection apparatus includes a window to transmit the light emitted from a LED module array located outside the conduit into the liquid within the conduit. The window may be located at one end of the conduit.

Figure 2A:
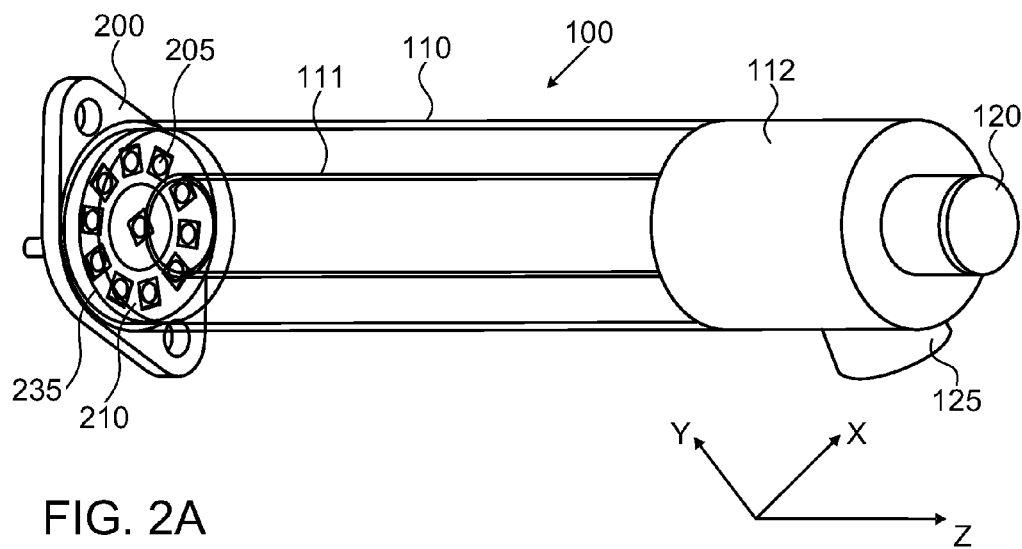
FIG. 2A is an illustration of an exemplary UV liquid treatment apparatus according to some embodiments of the invention.

FIG. 2A conceptually illustrates a UV liquid treatment apparatus according to some demonstrative embodiments of the invention. An apparatus 100 may include a conduit 110 for carrying the liquid, an inlet 120 to receive liquid to be treated and an outlet 125 to discharge treated fluid. Conduit 110 may be designed to define a plurality of liquid flow paths between inlet 120 and the outlet 125. Apparatus 100 may further include an array of UV LED modules 205 to illuminate the liquid. UV LED module array 205 may be arranged on a curved surface 235 of an array holder 200 to generate a customized spatial light flux distribution within the conduit that produces a UV dose with a desired dose distribution function. Apparatus 100 may further include an optical window 210 between array 205 and the liquid in conduit 110.

Conduit 110 may include an internal inlet tube 111 positioned within conduit 110 and conduit end 112. Liquid may enter inlet tube 111 from liquid inlet 120. The liquid may flow via internal tube 111 towards holder 200 and then via a gap formed between tube 111 and conduit 110 towards liquid outlet 125. In some embodiments, conduit 110 and tube 111 may be cylindrical concentric tubes. In some embodiments, conduit 110 and internal tube 111 may be optically transparent, for example, transparent to UV light. Alternatively, conduit 110 may be at least partially coated with a reflective coating, for example, conduit end 112 that includes outlet 125 and inlet 120 may be coated with reflective coating. Conduit 110 and internal tube 111 may include an optically transparent material, for example, quartz or polytetrafluoroethylene. Optionally, conduit 110 may be located inside an outer tube or housing (not shown). The housing may include any material suitable for protecting conduit 110, for example, the outer housing may include various metals and alloys, ceramic materials and others. An air gap may be formed between conduit 110 and the housing.

Figure 2B:
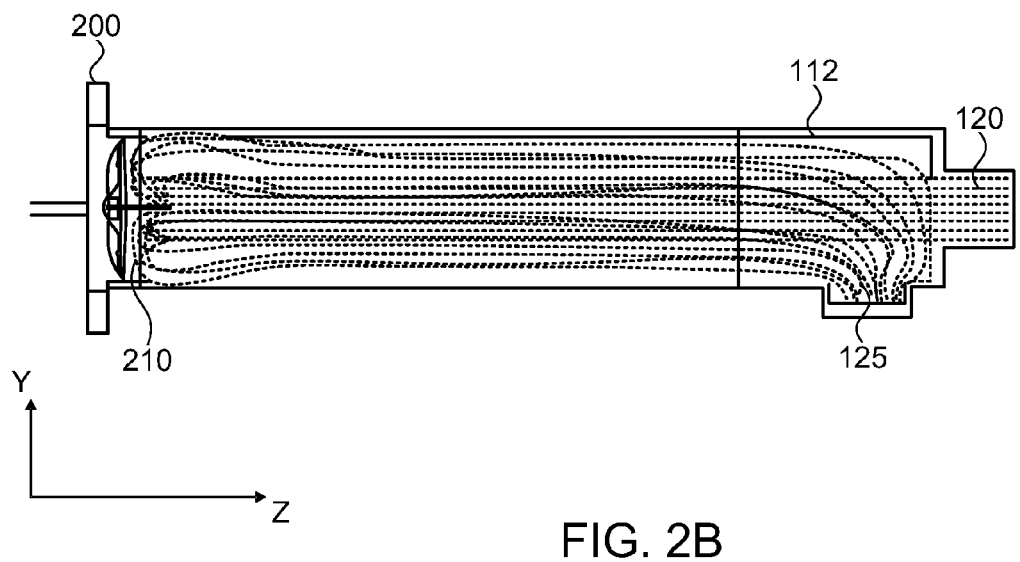
FIG. 2B is an illustration of a liquid flow pattern associated with the apparatus of FIG. 2A according to some embodiments of the invention.

Conduit 100 may be designed to define a plurality of liquid flow paths between inlet 120 and the outlet 125. For example, liquid to be treated may enter internal tube 111 via liquid inlet 120 and may flow toward window 210. Then, the liquid may flow in the opposite direction and may exit the conduit via liquid outlet 125. A computer simulation of exemplary flow paths of the liquid within apparatus 100 is illustrated in FIG. 2B. The liquid flow pattern is substantially stable inside the internal tube. Near window 210 the flow may slow down and before turning to flow towards outlet 125. During the turning the speed of the flow decreases, thus a larger volume of the liquid may absorb more light from UV LED module array 205. Further, the flow pattern in the area adjacent window 210 is symmetric.

Window 210 may separate UV LED module array 205 from the liquid flowing within conduit 110. Window 210 may be included in holder 200, as illustrated in FIGS. 2B and 2C. Alternatively, window 210 may be included in conduit 110, for example, such that window 210 and conduit 110 may be made from the same transparent material, optionally as one part. For example, conduit 110 and window 210 may be made from quartz as a single tube open at one end and closed by window 210 at the other end.

Window 210 may include at least one lens or any suitable optical element for generating the customized spatial light flux distribution within the conduit by directing most of the light rays emitted from LED module array 205 to be at a desirable entrance angle. For example, a desirable entrance angle may be such that would enable a light ray emitted from LED array 205 to strike the internal surface of conduit 110 at an angle larger than the critical angle for total internal reflection. In some embodiments, a portion of the external surface of conduit 110 may be covered with a reflective material such that light rays striking the internal surface of the coated portion would reflect back to the liquid utilizing the back-surface mirror effect. Window 210 may be designed to ensure that more that 50% of the light emitted from LED module array 205 would be totally-internally reflected in conduit 110.

According to embodiments of the invention, LED array may be designed and customized to generate a customized spatial light flux distribution within the conduit, for example, according to the geometrical characteristics of the conduit and optionally the characteristics of the liquid flow paths, to produce a UV dose with a desired dose distribution. Exemplary LED array 205 may include two or more LED modules positioned on the holder's surface that faces window 210. For example, in the exemplary LED array 205 eleven (11) LED modules are shown.

Figure 3A:
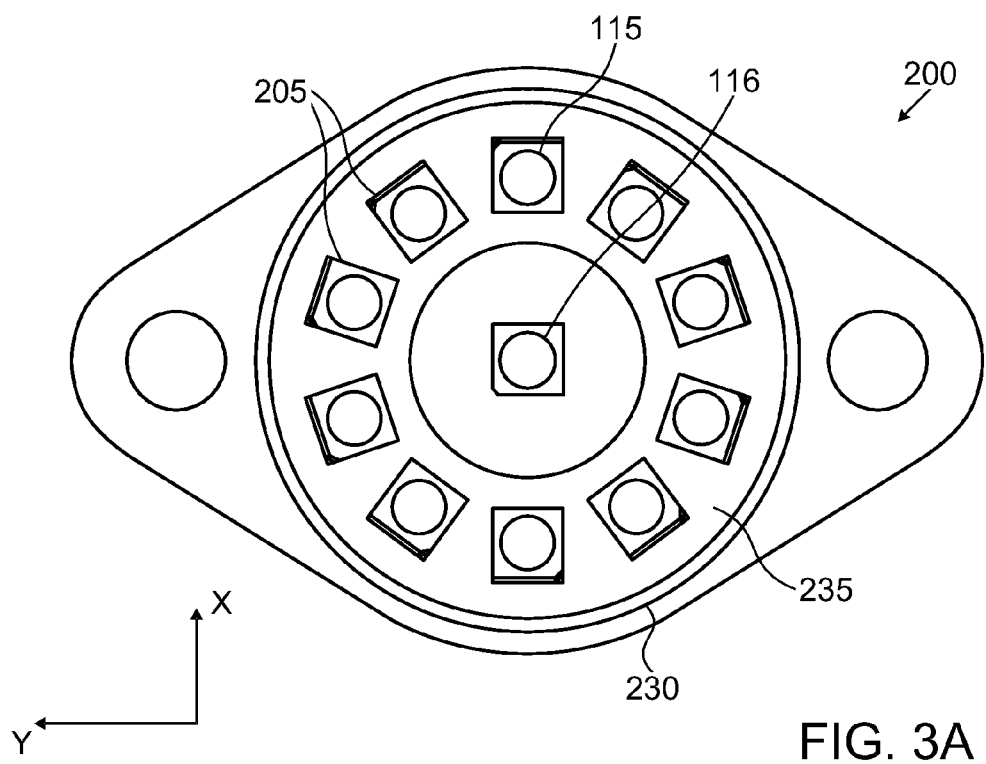
FIGS. 3A-3C illustrate top, perspective and side views of an exemplary LED module array holder according to some embodiments of the invention.
Figure 3B:
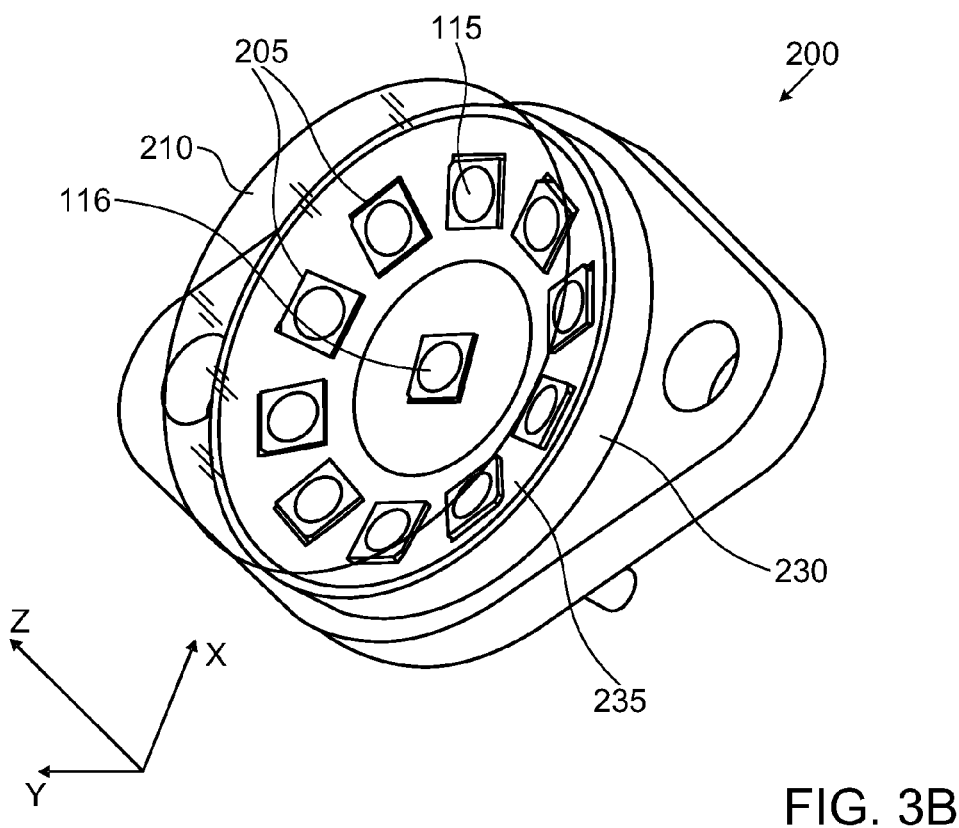
Figure 3C:
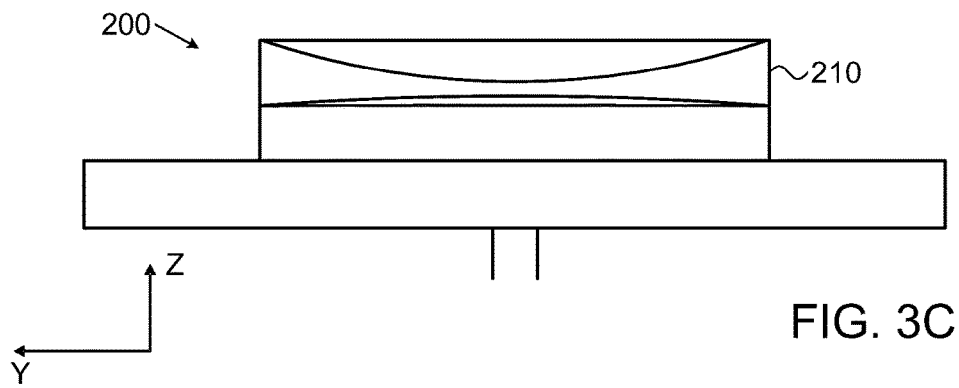

FIG. 3A-3C show a top view, perspective view and side view of an exemplary array holder, such as array holder 200 carrying LED module array 205, designed according to demonstrative embodiments of the invention. LED module array 205 may include a plurality of LED modules 115 and 116 positioned on a surface 235 of a plate 230. Surface 235 may be a flat or non-flat surface (e.g., curved) as demonstrated in FIG. 3B. Alternatively, surface 235 may have other geometrical shapes, for example pyramidal, with steps, etc. The geometrical shape of surface 235 may be such that LED modules 115 and 116 located on surface 235 may have a distinct placement in the X-Y plan and a title in the Z direction.

The position of each LED module in the array (e.g., the configuration of LED array) and the geometrical shape of surface 235 (e.g., the radius of curvature) may be determined such that UV light emitted from LED modules located on the non-flat surface would generate a customized spatial light flux distribution within conduit 110 that may produce a UV dose with a desired dose distribution. For example, light emitted from UV LED array 205 may propagate in conduit 110 substantially via total internal reflection and/or back-surface mirror effect. In some embodiments, surface 235 may be flat (planner). LED modules 115 may be placed symmetrically with respect to the central axis of conduits 110, as illustrated in FIG. 2B. Alternatively, LED modules 115 may be placed elsewhere in a non-symmetrical manner.

The dimension of LED holder 200 may be determined based on the dimension of conduit 110, for example, the inner and/or outer diameters of conduit 110 may define the diameter of plate 230. Surface 235 may be coated with reflective material. In the exemplary embodiment of FIGS. 3A-3C, ten (10) LED modules 115 are arranged in a circular arrangement around a central LED module 116. In this exemplary embodiment, each of LED modules 115 may be located at the peripheral area of surface 235 facing the gap between conduit 110 and internal tube 111. LED modules 115 are tilted relative to the X-Y plane due to the concave structure of surface 235 to ensure that most of the light emitted from LED modules 115 would enter the gap between conduit 110 and internal tube 111 within an angle range that would enable the light rays to be reflected back into the liquid from the walls of conduit 110.

Central LED module 116 may substantially illuminate the incoming liquid flow within internal tube 111. The position (e.g., placement) of each LED module 115 on surface 235 may be determined such that light emitted from each LED module 115 may propagate in conduit 110 substantially via total internal reflection. For transparent conduits having an external reflective coating, the location (e.g., placement) of each LED module 115 on surface 235 may be determined such that light emitted from each LED module 115 may propagate in conduit 110 utilizing the back-surface mirror effect.

LED holder 200 may further include window 210, illustrated in FIG. 3C. Window 210 may be UV light transparent. Window 210 may be flat or may include a lens for directing the light emitted from LED modules 115 and 116.

Figure 3D:
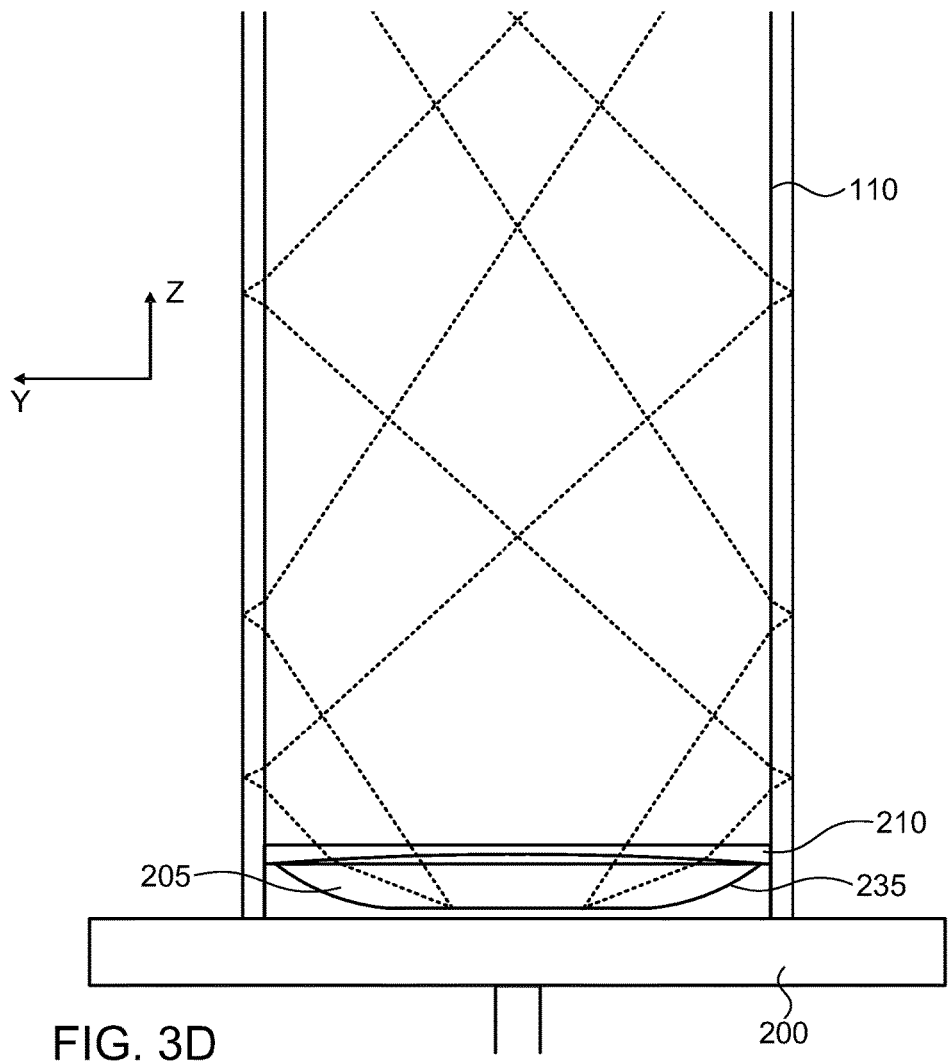
FIG. 3D is an illustration of spatial light flux distribution associated with the apparatus of FIG. 2A according to some embodiments of the invention.

FIG. 3D presents an illustration of computer simulation of a customized spatial light flux distribution within conduit 110 formed by UV light rays emitted from LED modules 115 and 116 located on surface 235. The simulation was done using Breault Research APEX ray-tracing software. The simulation shows that the radius of curvature of surface 235 and the position of each LED module 115 in array 205 on the surface were determined such that the majority of UV light rays emitted from the LED modules 115 would strike the walls of conduit 110 in an angle above the critical angle for total internal reflection (TIR) to be reflected back to the liquid more than one time. As would be realized by a person skilled in the art, window 210 may not influence the optical path of the rays emitted from LED modules 115 or alternatively may influence the optical path of the rays emitted from LEDs 115, for example, when window 210 includes a lens. Thus, in some embodiments, the geometrical dimensions of surface 235 (e.g., the radius of curvature) and the characteristics of the lens included in window 210 may be determined based on such simulations.

Figure 4A:
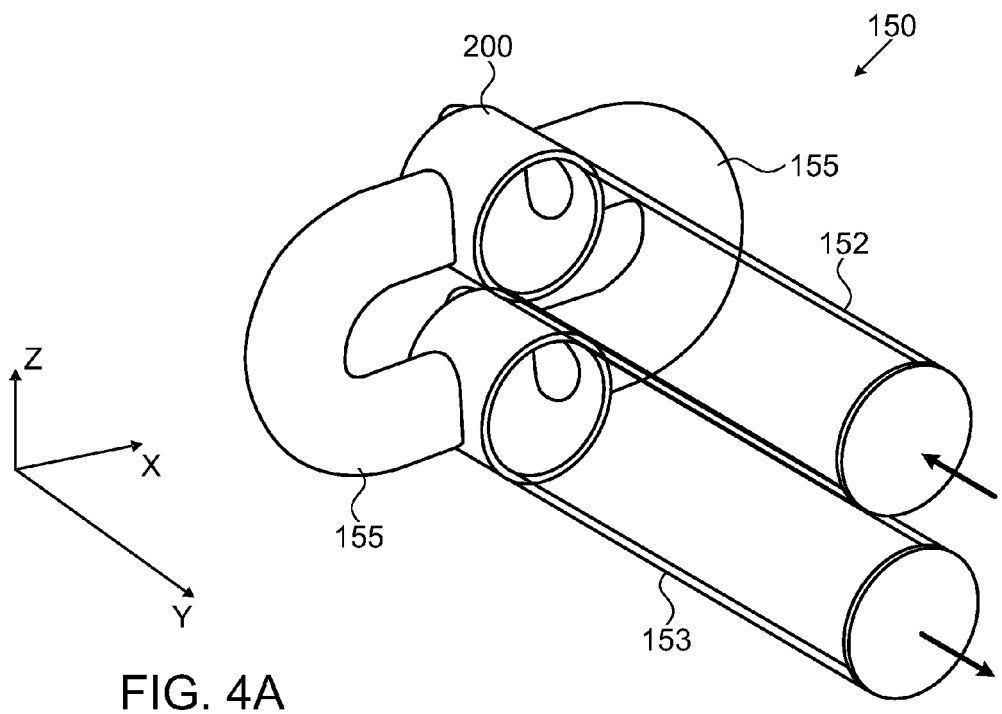
FIGS. 4A-4C are illustrations of an exemplary UV liquid treatment apparatus according to some embodiments of the invention.
Figure 4B:
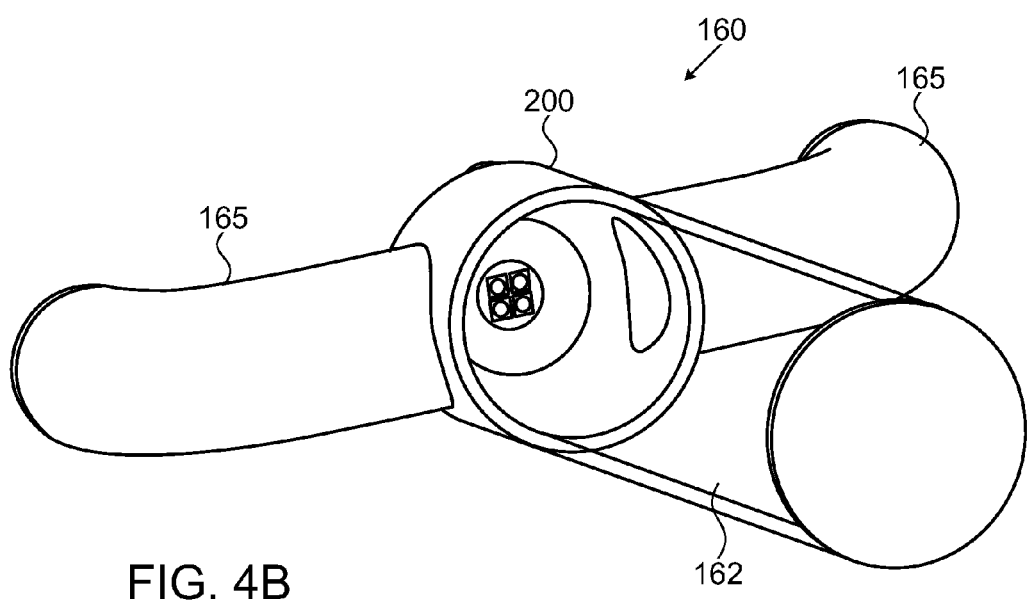

Reference is now made to FIGS. 4A and 4B, which illustrates another exemplary ultraviolet-based liquid treatment apparatus with an external LED array. An apparatus 150 may include a conduit having a first conduit section 152 and a second conduit section 153 first section 152 comprises the inlet and second section 153 comprises the outlet that are connected together by one or more tubes, for example, two tubes 155. Tubes 155 and sections 152 and 153 may comprise an optically transparent material. In some embodiments, sections 152 and/or 153 and/or tubes 155 may be at least partially coated with a reflective material, for example, tubes 155 and sections 152 and 153 may all be coated with the reflective material. At least one UV LED module array holder, such as holder 200, may be located externally to the liquid flow path of apparatus 150. For example, array holder 200 may be positioned at one end of section 152 adjacent to tube 155 externally to the liquid flow or at one end of section 153 adjacent tube 155 externally to the liquid flow. According to some embodiments, Apparatus 150 may comprise two array holders, each positioned adjacent one of section 152 and 153. Each of section 152 and 153 may include a transparent material.

Sections 152 and 153 may be similar (e.g., made from the same material and have the same dimensions) or may be different (e.g., made from different materials and/or having different dimensions). Liquid may enter apparatus 150 from an inlet in section 152 (see arrow) and may exit apparatus 150 from an outlet in section 153 (see arrows). The liquid may flow from section 152 to section 153 via tubes 155.

Figure 4C:
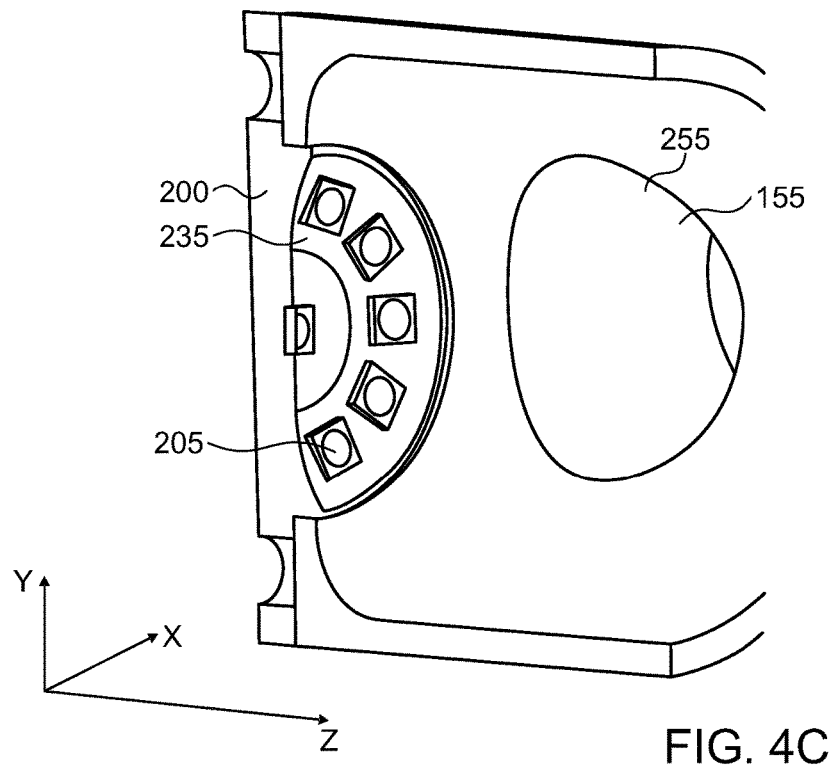

An exemplary UV module array holder is illustrated in FIG. 4C. Holder 200 may include UV module array 205 located on surface 235. Surface 235 may be any no-flat surface, for example, a curved surface. Each UV module may be located on surface 235 to generate a customized spatial light flux distribution within the conduit that produces a UV dose with a desired dose distribution function. Holder 200 may further include an optical window between array 205 and the liquid. Holder 200 may further include an entrance 255 for tube 155. In some embodiments, holder 200 may include two entrances 255 from two opposite sides of holder 200.

Figure 4D:
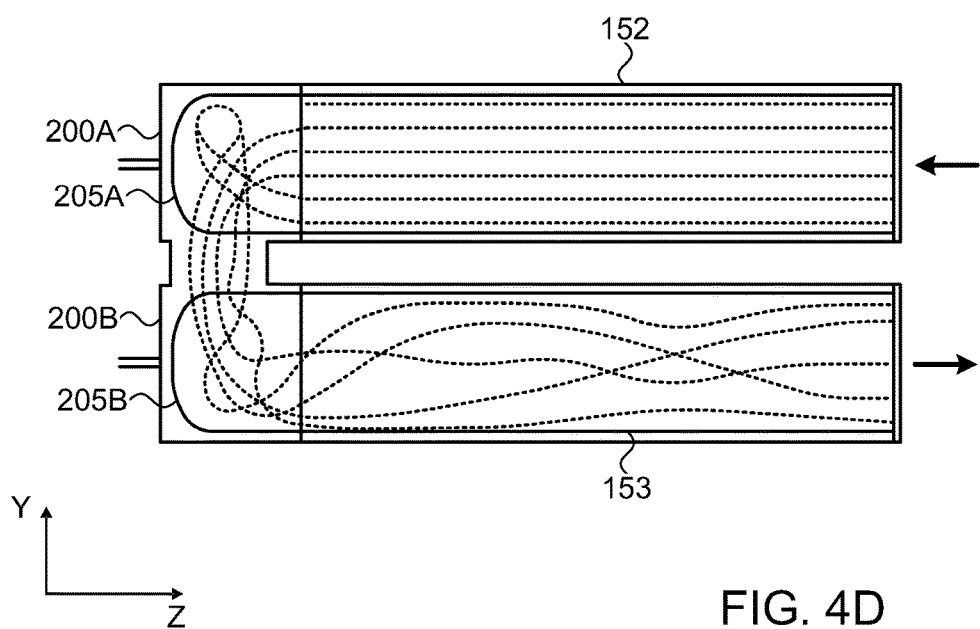
FIG. 4D is an illustration of a liquid flow pattern associated with the apparatus of FIG. 4A according to some embodiments of the invention.

A computer simulation of the spatial light flux distribution within apparatus 150 is illustrated in FIG. 4D. The simulation was done using FloWorks (Solifworks) CFD computational software. The liquid may enter apparatus 150 via the inlet in section 152 and flow towards LED holder 200A located at the end of section 152. Near the window of holder 200A (e.g., window 210), the flow may slow down and split between two tubes 155. The relatively slow flow allows light emitted from LED array 205A to be better absorbed by the liquid. The liquid may further enter section 153 from tubes 155. The divided flow may collide to form a single flow near the window of LED holder 200B, thus may be further slowdown allowing the light emitted from LED array 205B to be better absorbed by the liquid due to the flow rate and the short distance from the light source. The liquid may then exit via the outlet in section 153.

Holder 200A may be located at one end of section 152 facing the liquid flow. Additionally or alternatively, holder 200B may be located at one end of section 153 near the entrance of the liquid flow from tubes 155. The position and configuration of each of the LED modules in arrays 205A and 205B located on holders 200A and 200B may generate a customized spatial light flux distribution within the conduit, for example, such that light rays emitted from the LED arrays may propagate in section 152 and/or section 153 substantially via total internal reflection. For externally coated conduits, the position (e.g., placement) of the LED module on holder may be determined such that light emitted from each the LED may propagate in the at least partially coated conduit 110 utilizing the back-surface mirror effect or a combination of the back-surface mirror effect and TIR.

An additional exemplary UV liquid treatment apparatus with an external LED array is illustrated in FIG. 4B. Liquid to be disinfected may enter an apparatus 160 via a conduit 162 and flow towards a LED holder, such as LED holder 200. In the vicinity of LED holder 200, the flow of liquid may slow done and split into two flows that may exit apparatus 160 via pipes 165. The position and configuration of each of the LED modules on holder 200 may generate a customized spatial light flux distribution within the conduit, for example, such that light emitted from each of the LED's may propagate in conduit 162 substantially via total internal reflection. For externally coated conduits, the position and configuration of each of the LEDs located on holder 200 may be such that light emitted from the LED's propagate in conduit 162 substantially by utilizing the back-surface mirror effect. In some embodiments, a similar disinfecting effect may be achieved when the liquid enters apparatus 160 via at least one of pipes 165 and exits apparatus 160 via conduit 162.

Reference is now made to FIGS. 5A, 5B, 6A, 6B and 6C, which demonstrate some exemplary embodiments, in which the array holder is located inside the conduit, to be at least partially submerged in the liquid. The array holder may include first and second surfaces each comprising a UV LED module array positioned back to back, one to each other. The first and second surfaces may be curved surfaces. The array holder may be positioned inside the conduit perpendicular to a longitudinal axis of the conduit such that a first UV LED module array positioned on the first curved surface would illuminate a first portion of the conduit and a second UV LED module array positioned on the second curved surface would illuminate a second portion of the conduit. According to some embodiments, the disinfection apparatus may include a plurality of LED holders positioned within the conduit along the liquid path, each LED holder may include one or two LED module arrays.

Figure 5A:
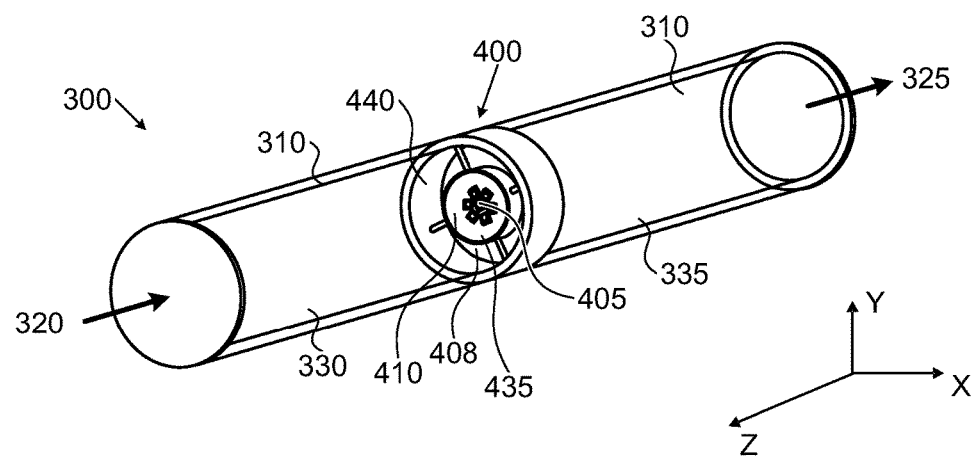
FIG. 5A illustrates an exemplary UV liquid treatment apparatus according to some embodiments of the invention.
Figure 5B:
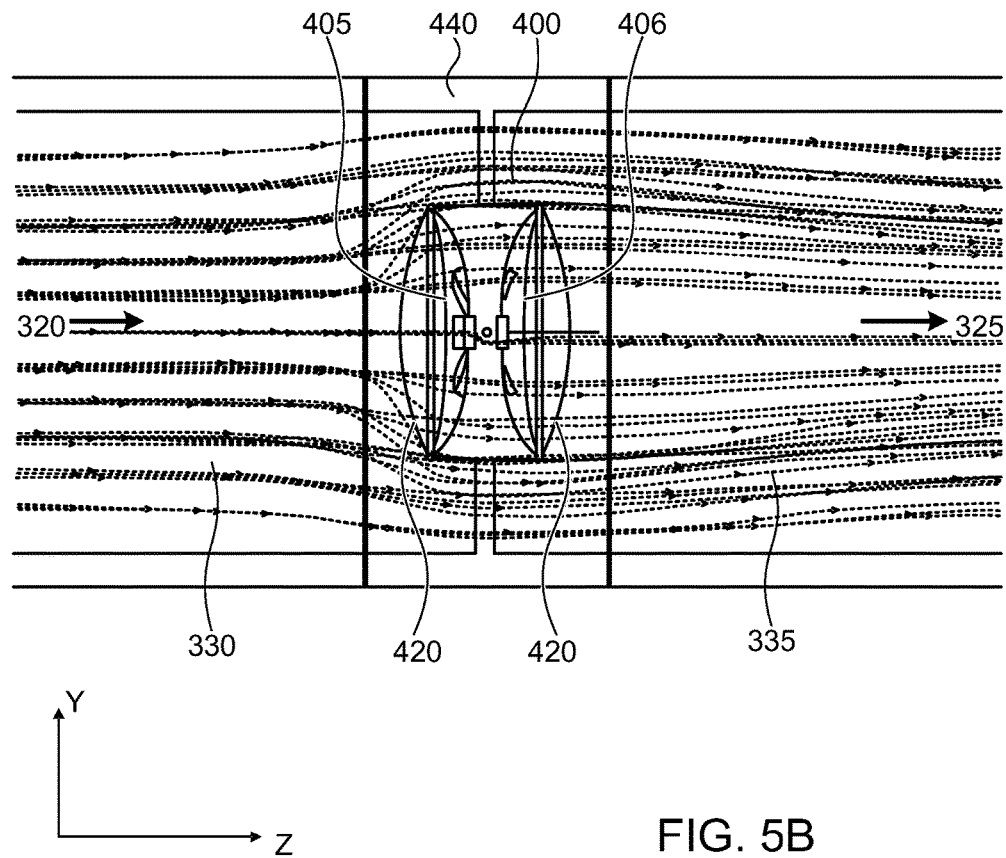
FIG. 5B is an illustration of a liquid flow pattern associated with the apparatus of FIG. 5A according to some embodiments of the invention.

Reference is now made to FIGS. 5A and 5B that presents an illustration of an exemplary UV liquid treatment apparatus 300, according to some embodiments of the invention. An apparatus 300 may include a conduit 310 for carrying liquid, a liquid inlet 320 to receive liquid to be treated and a liquid outlet 325 to discharge the treated liquid. Apparatus 300 may further include a UV LED module array holder or holding unit 400, one or more UV LED module arrays 405 having a plurality of UV LED modules arranged on one or more curved surfaces 435 of array holder 400.

Conduit 310 may include two conduit portions 330 and 335 joined together or defined by array holder 400. Array holder 400 may be connected to a first conduit portion 330 from one side and to a second conduit portion 335 from the other side. Conduit 310 may include any material suitable for holding liquids, for example, stainless steel, quartz, various polymers, or the like. An exemplary conduit 310 may include material transparent to UV light. In some embodiments, conduit portions 330 and/or 335 may be UV transparent section at least partially covered with a reflective coating on their external surfaces. In some embodiments, the entire conduit may be externally covered with a reflective coating.

Array holder 400 may include a peripheral element 440 and an array carrier 410 located inside conduit 310 to carry one or more UV LED module arrays, such as arrays 405 and/or 406. LED module arrays 405 and/or 406 may be positioned back to back on surfaces 435 and/or 436 respectively (as illustrated in FIG. 6B). Surfaces 435 and 436 may be flat or non-flat (e.g., curved). UV LED module array 405 may be positioned on first surface 435 to illuminate first portion 330 of conduit 310 and UV LED module array 406 may be positioned on second surface 436 to illuminate second portion 335 of conduit 310.

Array carrier 410 may be positioned inside conduit 310 perpendicular a longitudinal axis of the conduit and to the direction of flow of the liquid. Array carrier 410 may be connected to peripheral element 440 by any suitable mechanism provided that there would be at least one liquid path 408 from inlet 320 to outlet 325. In the exemplary embodiment of FIG. 5A, Array carrier 410 is connected to LED holding unit with 4 branch joints forming four (4) passages 408 for the liquid flow.

Array holder 400 may further include optically transparent covers 420 (illustrated in FIG. 6B) each covering surfaces 435 and 436 in order to protect the UV LED module arrays. Cover 420 may include an optical lens for further directing the light rays emitted from each LED 115 and 116 (illustrated in FIG. 6A). In some embodiments, peripheral element 440 may be shaped as a ring 440 connecting conduit sections 330 and 335 of conduit 310. Peripheral element 440 may be coated with optically reflective coating.

Conduit 310 may include an optically transparent material and may further be located inside a housing (not illustrated) suitable for protecting and/or supporting conduit 310. For example, the housing may include various metals and alloys, ceramic materials, etc.

In some embodiments, array carrier 410 may include a second LED module array 406 (illustrated in FIG. 5B) located on a second surface 436 of array carrier 410 positioned substantially perpendicular to longitudinal axis of conduit 310 in the X-Y plane and to the direction of liquid flow and facing second portion 335 so as to emit light (e.g., UV light) to the second portion 335 of conduit 310. First LED module array 405 and second LED module array 406 may be located back to back, one with each other on array carrier 410 as illustrated in FIG. 5B.

FIG. 5B is an illustration of a computer simulation of liquid flow paths in apparatus 300, according to some embodiments of the present invention. The computer simulation was done using the FloWorks (Solifworks) CFD computational software. Liquid may enter apparatus 300 from inlet 320 and may exit the apparatus via outlet 325. The liquid flow in the vicinity of array carrier 410, with very little destruction. For example, the laminar flow illustrated at FIG. 5B, may be kept, although the liquid may interact with array carrier 410.

Figure 6A:
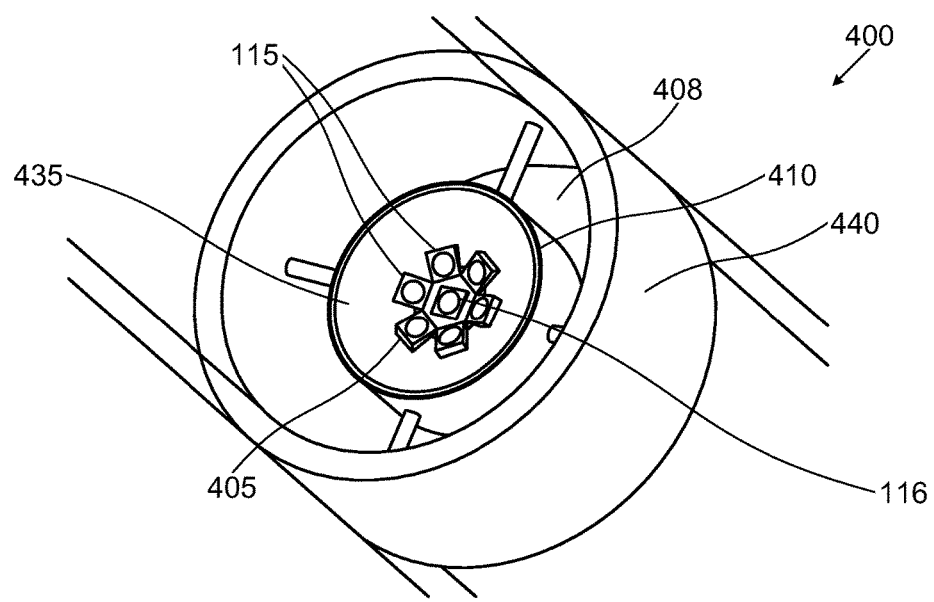
FIG. 6A is an illustration of an array holder for UV LED module array according to some embodiments of the invention.
Figure 6B:
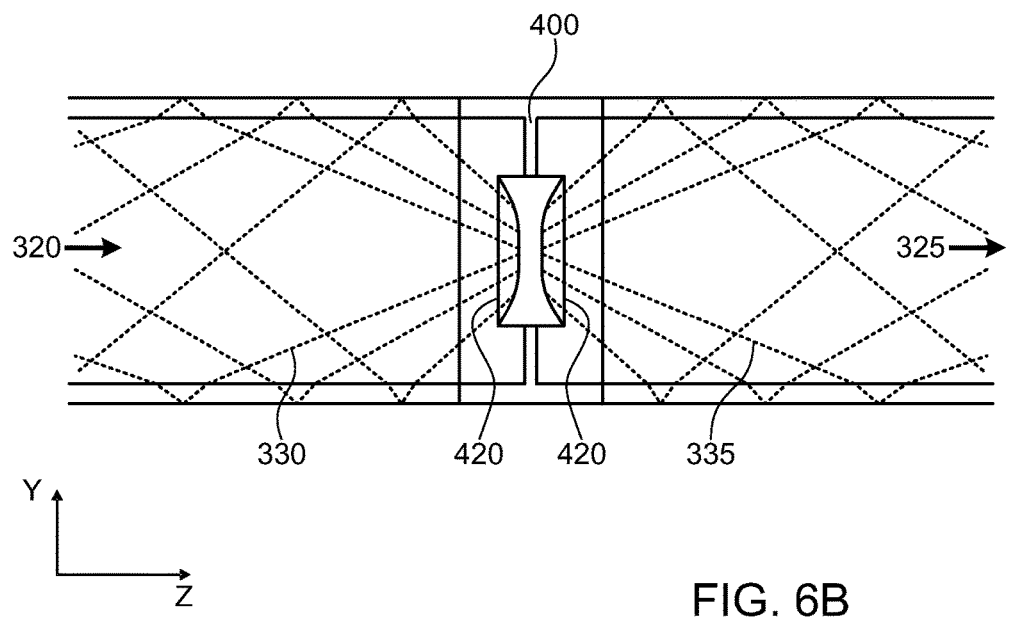
FIG. 6B is an illustration of spatial light flux distribution associated with the apparatus of FIG. 5A according to some embodiments of the invention.

Reference is now made to FIG. 6A illustrating an array holder, such as array holder 400 comprising a peripheral element, such as element 440, an array carrier, such as array carrier 410, according to some embodiments of the invention. Array carrier 410 may include LED module array 405 comprising two or more LED modules, such as LED modules 115 and LED module 116. The LED modules are located on a surface 435 included in carrier 410. For example, Array carrier 410 may include seven (7) LED modules. Surface 435 may be a flat or non-flat surface, for example, curved-like surface as illustrated in FIG. 6A. Surface 435 may have the same properties as was disclosed with respect to curved surface 235 illustrated in FIG. 3B. LED modules 115 located on surface 435 may have a distinct placement or positioning in the X-Y plan and a title in the Z direction. Holder 400 may further at least one liquid path 408 to allow a liquid flow from one side of the holder to the other.

Figure 6C:
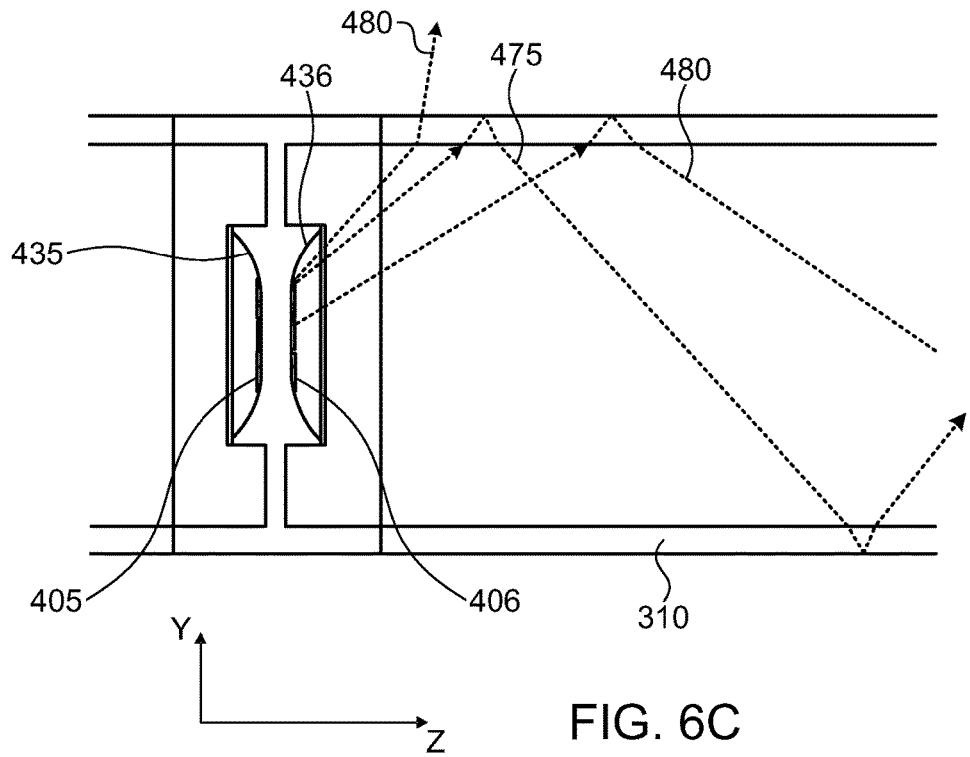
FIG. 6C is an illustration that demonstrates Total internal reflection and helpful in understanding embodiments of the invention.

The position of each LED module in the array (e.g., the configuration of LED array) and the geometrical dimensions (e.g., radius of curvature) may be determined to generate a customized spatial light flux distribution within the conduit that matches the liquid flow paths so as to obtain a desired UV dose distribution. For example, UV light emitted from each LED module 115 or 116 located on non-flat surface 435 may propagate in the conduit substantially via total internal reflection and/or back-surface mirror effect. LED modules 115 may be placed symmetrically with respect to the longitudinal axis of conduit 310 and LED module 116 may be located at the longitudinal axis of conduit 310, as illustrated in FIG. 6A. Array carrier 410 may further include second array 406 placed on surface 436 located opposite (back to back) to array 405 placed on surface 435 (as illustrated in FIG. 6C). Surface 436 may be a flat surface or may be a non-flat surface, for example the curved surface illustrated.

The number of LED modules located on surface 436 may be the same or may be different from the number of LED modules located on surface 435, for example, array 406 may not include central LED module 116. The position of each LED module 115 in array 406 and the geometrical dimensions (e.g., the radios of curvature) of surface 436 may generate a customized spatial light flux distribution within first portion 330 and second portions 335 of conduit 310. The dimension of surface 436 may be the same as of surface 435 or may be different from surface 435. The number of LED modules in array 406 and/or the position (in the X, Y and Z directions) may be the same or may be different from the number of LED modules and their positions in array 405.

FIG. 6B presents an illustration of a computer simulation of a customized spatial light flux distribution within the conduit that includes UV light rays emitted from LED modules 115 and 116 located on surfaces 435 and 436. The simulation was done using the Breault Research APEX ray-tracing software. The simulation shows that the radius of curvature of surfaces 435 and 436 and the position of each LED module on those surfaces were determined such that the majority of UV light rays emitted from each LED modules would strike the surface of conduit 310 in an angle above the critical angle for TIR and may reflect back to the liquid. Additionally, the simulation may include protective covers 420. Protective covers 420 may not influence the optical path of the rays emitted from LED modules 115 and 116, for example when the surface of the cover is flat as illustrated in FIGS. 6B and 6C, or may influence the optical path of the rays emitted from LED modules 115 and 116, for example, when protective covers 420 include a lens.

FIG. 6C is an illustration of the optical path and propagation of three (3) exemplary UV light rays 470, 475 and 480. Rays 470 and 475 presents the majority of rays emitted from LED module array 406 and striking the surface of conduit 310 at an angle above the critical angle for TIR. Ray 480, as an example, for a ray that strikes the surface conduit 310 at an angle above the critical angle, for TIR and escapes from the conduit. LED arrays 406 and 405 and surfaces 435 and 436 may be designed to minimize the number of rays, such as ray 480. In some embodiments, the position of each of the LED modules in the LED module arrays 405 and 406 may be pre-designed such that the light emitted from each of the LED modules may propagate in the conduit substantially via total internal reflection and/or back-surface mirror effect. The LED array may be located within or outside the conduit.

For externally coated UV transparent conduits (coated with a reflective coating), the position of each of the LED modules in the LED array may be pre-designed such that the light emitted from each of the LED modules may propagate in the conduit substantially via back-surface mirror effect. The geometry of the holder, the surface and the conduit and the position of the LED modules at the array relative to each other may be such that the majority of light rays emitted from each of the LED modules may strike at least a portion of the internal surface of the conduit, coated with reflective coating, at various angles to achieve a uniform dose distribution utilizing the back-surface mirror effect.

In some embodiments, the disinfection apparatus, for example apparatus 100, 150, 160 or 300 may be installed in the vicinity of a point of use, for example, at a domestic water system. Point of use disinfection systems may be located below a sink (e.g., kitchen sink), as a part of the faucet or in any other location along the water pipe. In such systems, it may be required to disinfect any amount of water going from the pipe to the end user, thus the disinfection apparatus should be operated upon opening of the faucet. Some embodiments of the invention may include a switch configured to close an electric circuit upon exposure to a water flow.

The conduit may include material transparent to light, for example a UV-transparent material, such as, for example, quartz or Polytetrafluoroethylene. A transparent material may be defined as any material that transfers more than 50% of the light at the spectral range between 200-320 nm. The conduit may be surrounded by a protective housing to protect the quartz conduit. The housing may be in the form of a tube or pipe and may absorb and/or reflect light (e.g., UV light). Non limiting examples for the housing walls may include metallic walls such as for example, stainless steel walls, non-metallic walls, such as for example, concrete or plastic walls and others.

An air gap may be formed between the housing and the conduit. According to some embodiments, the liquid flowing within the transparent material may act as a waveguide and at least part of the light, for example, at least half of the emitted light intensity (e.g., UV intensity), may be totally internally reflected at the interface between the optically transparent conduit and the medium surrounding it. According to embodiments of the invention, at least 50% of the emitted light intensity may be totally-internally reflected at the interface between the optically transparent sleeve and medium surrounding it.

According to some embodiments, a portion of the external surfaces of the transparent conduit may be coated with a reflective coating to reflect back to the water UV light rays that do not undergo total internal reflection by utilizing the back-surface mirror effect. The reflected coating may cover selected portions of the conduit, for example, the end side of the conduit opposite the LED array, or one or more reflective coating rings having any desired width and located at any point along the conduit. In some embodiments, the reflected coating may cover the entire external surfaces of the transparent conduit such that light rays may propagate within the liquid utilizing the back-surface mirror effect generated by the reflective coating.

Figure 7:
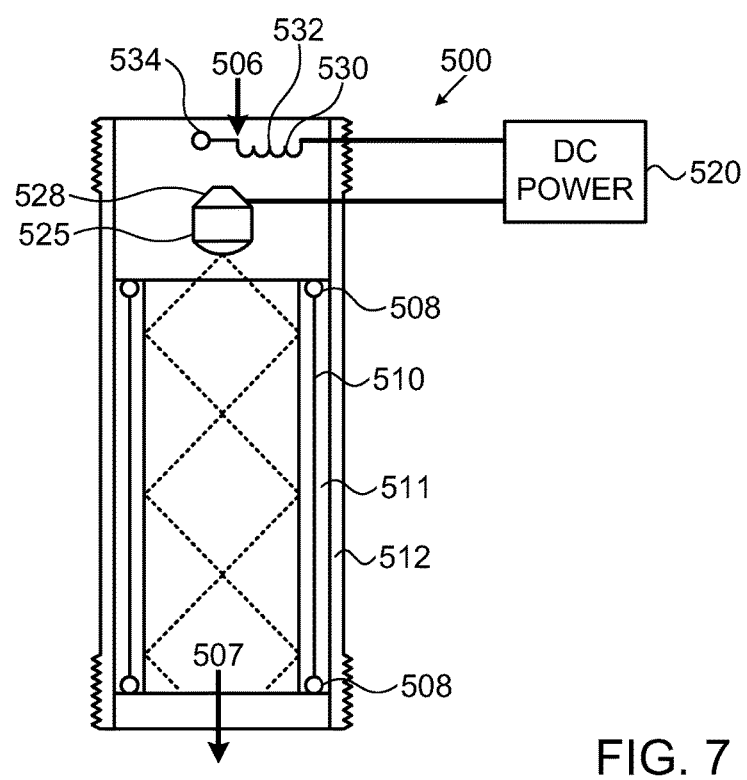
FIG. 7 is an illustration of an exemplary UV liquid treatment apparatus according to some embodiments of the invention.

An illustration of an example for such a switch is shown in FIG. 7. The switch of FIG. 7 is given as an example for switches activated by water flow only. Embodiments of the present invention are not limited to any use of any particular switch. FIG. 7 is an illustration of an exemplary apparatus 500 for disinfecting liquid in the vicinity of a water faucet, according to some embodiments of the invention. Apparatus 500 may include a UV transparent water conduit 510 and an outer opaque pipe 512. In some embodiments, at least a portion of conduit 510 may be coated with reflective coating. A gap 511 may be formed between conduit 510 and pipe 512. Gap 511 may be sealed from water using gaskets 508, such as O-rings. Water may enter apparatus 500 from an inlet 506 and may exit from an outlet 507. Apparatus 500 may further include a LED array 525 comprising a first switch 528, a second switch 530 and a power source or power supply unit 520, such as a DC power source.

LED module array 525 may be located on a LED holder, for example holder 400 or holder 200. Array 525 may be electrically connected to switch 528, which may be a magnetic switch. The LED modules in array 525 may be powered by a DC current from DC power source 520 when expose to a flow of water. DC power source 520 may be in electrical connection with first switch 528 and with second switch 530. Second switch 530 may include a flexible arm 532 (e.g., a spring) and a magnet 534. When water flows from inlet 506 towards LED array 525, flexible arm 532 may bend in the flow direction and may cause magnet 534 to be in an electrical contact with switch 528, closing an electrical circuit and instantly lightening LED array 525. Flexible arm 532 may be mounted to pipe 512 at one end, as illustrated for example in FIG. 5. Optionally, flexible arm 532 may be mounted onto pipe 512 at both ends of the flexible arm. Flexible arm 532 may include any flexible element for example, coil spring, cantilever spring, leaf spring, etc. Flexible element 532 may be electrically conductive or may include electrically conducive element(s) and may be in electrical connection with power source 520.

Dose Distribution Simulation Results

Simulated results showing the UV dose distribution in [mJ/cm$^2$] were obtained using Numerical Simulation code. The geometrical dimensions of apparatuses 100 and 300 were used as the base for the simulations. For each apparatus two LED array configurations were simulated: a commercial flat UV LED array and a UV LED array with a concave surface having the LED module arrangement illustrated in FIGS. 2B and 4A. The number of UV LED modules in each array (commercial and curved) and/or the amount of UV power applied to the water was the same for each simulation. Additionally, the average dose in [mJ/cm$^2$], the track uniformity factor and the DSL value were calculated for each simulation.

The track uniformity factor (TUF) may be calculated using the following equation:

$$TUF \equiv \frac{D_{eq}}{D_{av}} \quad (1)$$

where $D_{av}$ is the Track-Average Dose and $D_{eq}$ may be calculated from equation (2).

$$D_{eq} = -\frac{D_{1log} \cdot \ln\left[\frac{N_M}{N_{M-total}}\right]}{a} \quad (2)$$

where $D_{1log}$ is the dose required for achieving one-log of inactivation (of a specific microbe), $N_M$ is the number of active microbes that will be inactivated in a particular system, $N_{M-total}$ is the total (initial) number of pathogens\microbes and $a=\ln(10)=2.3$.

The TUF values range from 0 to 1. In some embodiments, TUF values should be as high as possible. The DSL is a value defining the difference between the minimum dose $D_{min}$ and the average dose $D_{av}$. DSL values range between 0 to 1. In some embodiments, DSL values may be as low as possible. The DSL may be calculated using equation (3).

$$DSL \equiv \frac{D_{av} - D_{min}}{D_{av}} \quad (3)$$

Figure 8A:
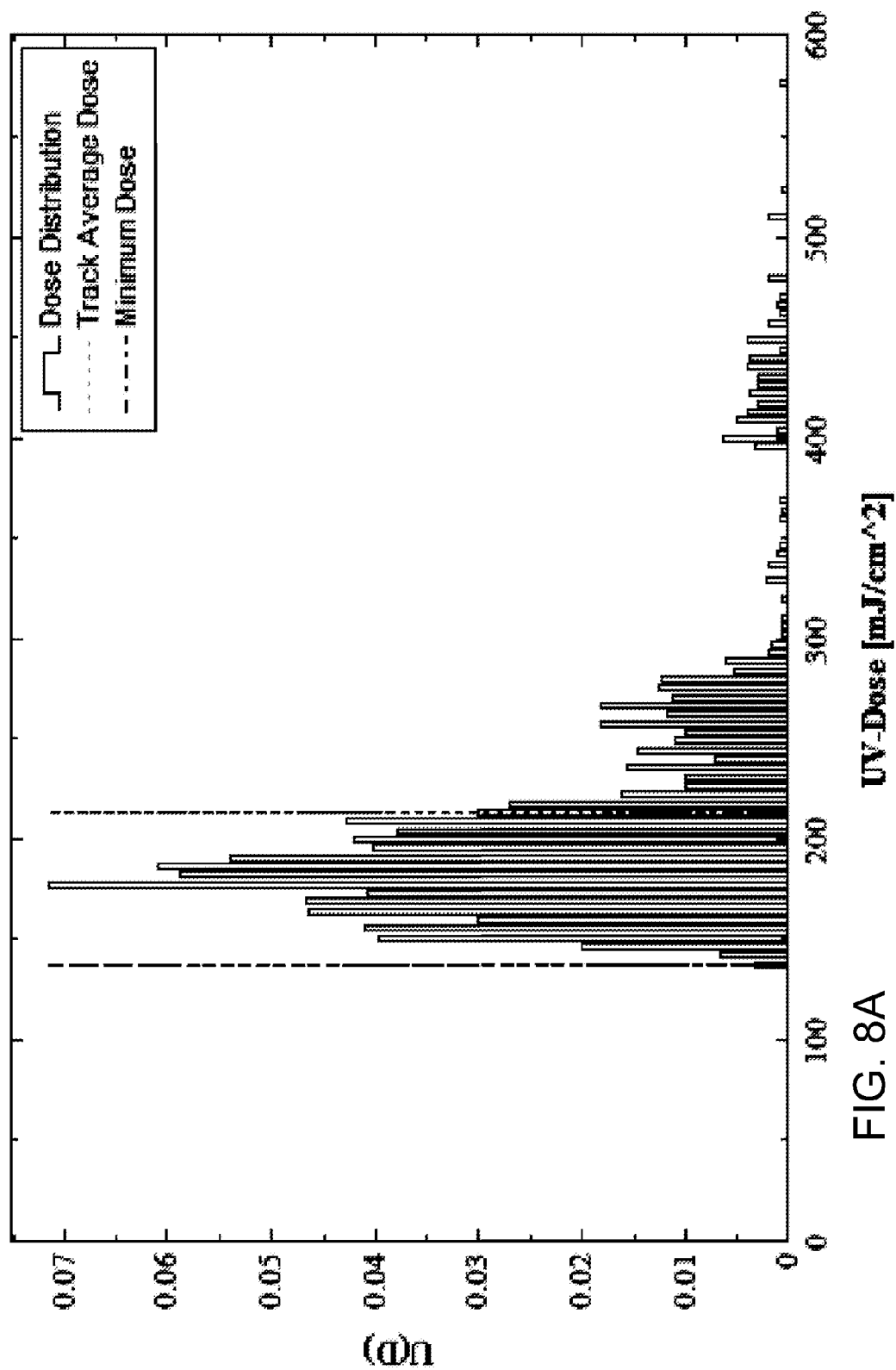
FIGS. 8A and 8B are simulated UV-dose distribution diagrams according to some embodiments of the invention.
Figure 8B:
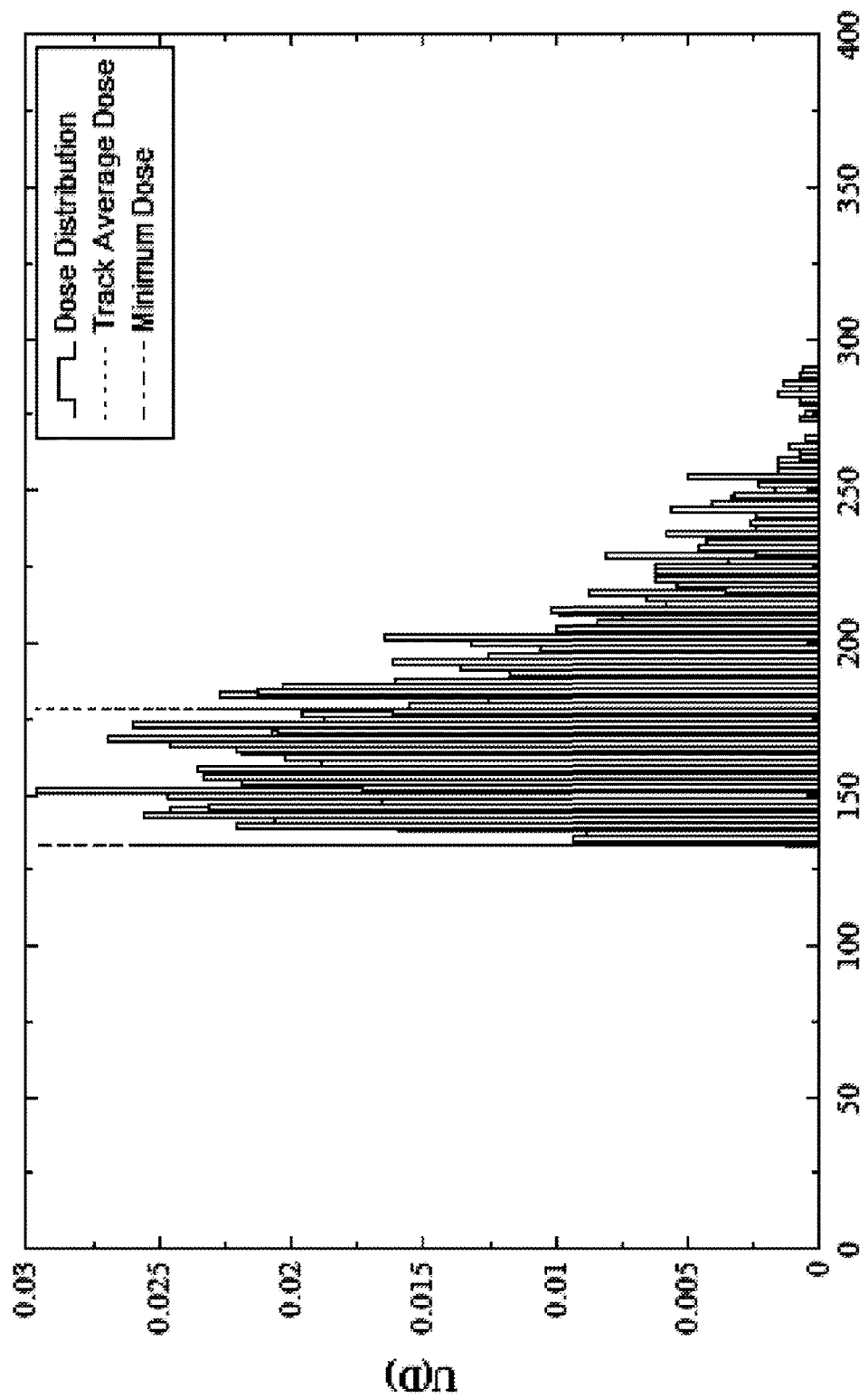

FIG. 8A presents a dose distribution diagram derived from computerized simulations for an apparatus having a commercial LED array located on a flat surface FIG. 8B presents a dose distribution diagram derived from computerized simulations for an apparatus according to embodiments of the invention, such apparatus 100 comprising UV LED module array 205 located on a curved surface of holder 200 (as illustrated in FIG. 2B). The two LED arrays were located externally to conduit 110 behind window 210. The dose distribution simulation presented in FIG. 8A shows a wide distribution with dose values from 138-580 [mJ/cm$^2$]. The average dose was 214 [mJ/cm$^2$] however the track uniformity factor was relatively low 0.77 due to the wide distribution. The narrower the distribution the higher the track uniformity factor the better is the energy delivery efficiency to the flow, i.e., the spatial light flux distribution is such that all portions of the conduit are illuminated with approximately the same amount of UV energy thus having the same disinfection. The DSL was 0.35. The dose distribution simulation presented in FIG. 8B shows much narrower distribution with dose values from 134-290 [mJ/cm$^2$]. The average dose was 179 [mJ/cm$^2$] however the track uniformity factor was much higher 0.86 and the DSL was much lower 0.25. This result was obtained due to the use of holder 200 and the placement of each LED element on the curved surface of holder 200 such that light emitted from each element propagates in conduit 110 via total internal reflection.

Figure 9A:
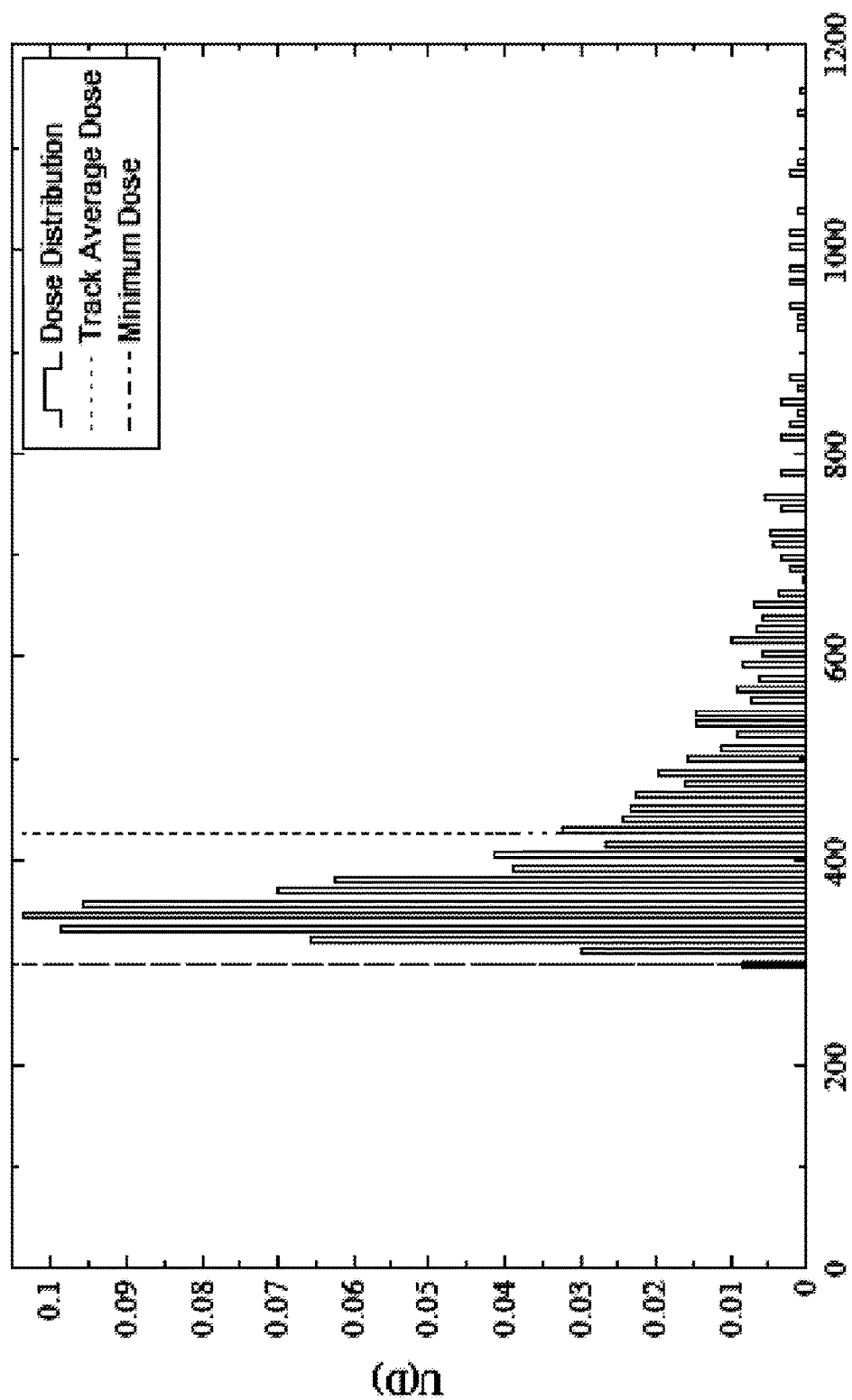
FIGS. 9A and 9B are simulated UV-dose distribution diagrams according to some embodiments of the invention.
Figure 9B:
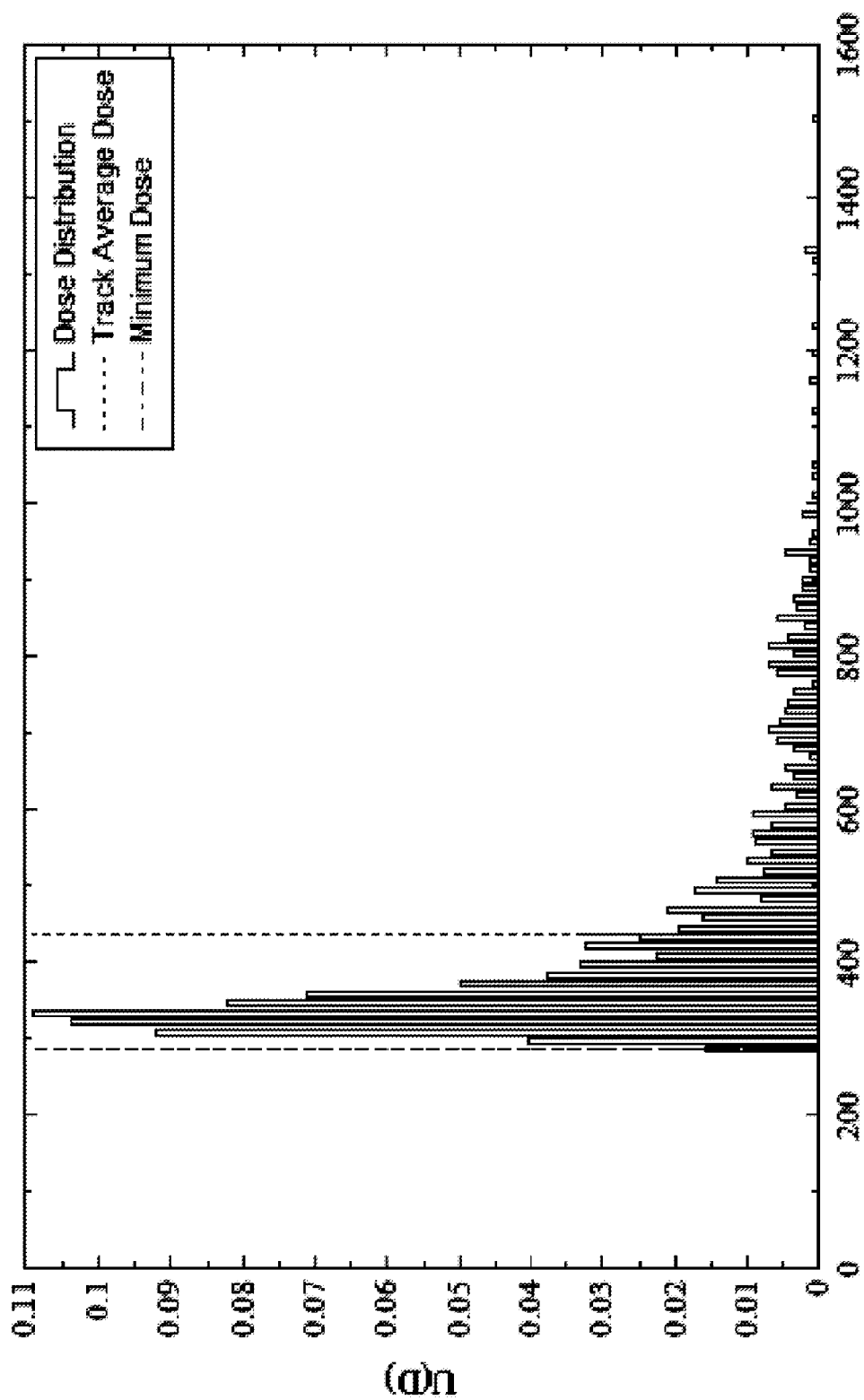

FIGS. 9A and 9B presents simulation of dose distribution diagrams of apparatus 300 comprising two pairs of LED arrays placed back-to-back inside conduit 310: a) pair of commercial LED arrays located at the center of holder 400 and arrays 405 and 406 located on holder 400 (as illustrated in FIGS. 5A, 5B and 6A) respectively. The dose distribution simulation presented in FIG. 9A shows a dose distribution having a high average dose of 439 [mJ/cm$^2$] with a medium track uniformity factor of 0.71 and a low DSL of 0.3. The high average dose may be related to the position of the LED array inside the water flow in the conduit, according to some embodiments of the invention, thus all the UV light emitted from the LED modules is transformed into the water, regardless of the configuration and position of the LED modules on the array. The average dose is approximately twice as much as the dose transferred to the water using the apparatus 100 with commercial LED array although the amount of UV power transfer into the water was approximately the same. The relatively low track uniformity factor of 0.71 may be related to the non-optimal configuration of LED modules in the commercial array that do not support any particular form of light propagation in the conduit. The dose distribution simulation presented in FIG. 9B shows a dose distribution having a high average dose of 428 [mJ/cm$^2$] with higher track uniformity factor of 0.77 with respect to the distribution showed in FIG. 8A, but a little higher DSL of 0.35. Again, the high average dose may be related to the position of the LED array inside the water flow in the conduit, according to some embodiments of the invention. The higher track uniformity factor of 0.77 may be related to the optimized location of the LED modules placement on holder 400 that supports total internal reflection. It may be concluded that the main effect presented at FIGS. 9A and 9B may be related to the insertion of two LED arrays into the water flow such that the first UV LED array located inside the water flow may lighten a first portion of the conduit in a direction facing the water flow and the second UV LED array located inside the water flow may lighten a second portion of the conduit in a direction of the water flow.

While certain features of the invention have been illustrated and described herein, many modifications, substitutions, changes, and equivalents may occur to those of ordinary skill in the art. It is, therefore, to be understood that the appended claims are intended to cover all such modifications and changes as fall within the true spirit of the invention.

What is claimed is:

1. An ultraviolet (UV) liquid treatment apparatus comprising:
   a UV transparent conduit for carrying flowing liquid comprising an inlet to receive liquid to be treated and an outlet to discharge treated liquid, the apparatus is configured such that when the liquid flows in the conduit, the liquid acts as a waveguide, whereby at least part of the UV light is totally internally reflected; and
   an array holder positioned inside the conduit and comprising first and second curved surfaces being located back to back one to each other, the array holder being in an X-Y plane substantially perpendicular to a longitudinal axis of the conduit,
   wherein the first curved surface comprises a first UV light emitting diode (LED) module array that illuminates a first portion of the conduit having the inlet and having an LED module tilted with respect to the X-Y plane and the second curved surface comprises a second UV LED module array that illuminates a second portion of the conduit having the outlet and having an LED module tilted with respect to the X-Y plane,
   wherein each of the first and second UV LED module arrays comprises a plurality of UV LED modules arranged on a respective one of the curved surfaces in pre-designed positions so as to increase the efficiency of the UV liquid treatment and generate a customized spatial light flux distribution such that the majority of UV light rays emitted from the LED modules strike a surface of the conduit in an angle above the critical angle for total internal reflection (TIR) and propagate in the conduit via TIR,
   wherein the conduit comprises first and second UV transparent conduit portions joined together by the array holder.

2. The UV liquid treatment apparatus of claim 1, wherein the curved surfaces are concave-like surfaces.

3. The UV liquid treatment apparatus of claim 1, wherein the curved surfaces are conic-like surfaces.

4. The UV liquid treatment apparatus according claim 1, wherein dimensions of the curved surfaces of the array holder are determined according to the customized spatial light flux distribution.

5. The UV liquid treatment apparatus of claim 1, wherein a radius of curvature of the curved surfaces of the array holder is determined based on the customized spatial light flux distribution.

6. The UV liquid treatment apparatus of claim 1, wherein a position of the UV LED modules on the array holder is determined based on the customized spatial light flux distribution.

7. The UV liquid treatment apparatus of claim 1, further comprising:
   a power source to power the UV LED module arrays; and
   a switch activated by a liquid flow, the switch is activated when the liquid flows in the conduit, connecting the power source to the UV LED module arrays.

8. The UV liquid treatment apparatus of claim 1, wherein the first conduit portion comprises the inlet and the second conduit portion comprises the outlet.

9. The UV liquid treatment apparatus of claim 1, wherein each of the UV LED modules comprises a plurality UV light emitting diodes.

10. The UV liquid treatment apparatus of claim 1, wherein UV LED module arrays emits at a wavelength range of between 200 to 320 nm.

11. The UV liquid treatment apparatus of claim 1, wherein the array holder comprises a peripheral element and UV light emitting diode (LED) array carrier, wherein the array carrier comprises the first and second curved surfaces wherein rays emitted from the first UV LED module array positioned on the first curved surface strike the first transparent portion of the conduit and rays emitted from the second UV LED module array positioned on the second curved surface strike the second transparent portion.

* * * * *